(12) United States Patent
Snow et al.

(10) Patent No.: US 9,295,573 B2
(45) Date of Patent: Mar. 29, 2016

(54) SELF-ADJUSTING GASTRIC BAND HAVING VARIOUS COMPLIANT COMPONENTS AND/OR A SATIETY BOOSTER

(71) Applicant: Apollo Endosurgery, Inc., Austin, TX (US)

(72) Inventors: Sean Snow, Carpinteria, CA (US); Marcos Borrell, Goleta, CA (US); Ahmet Tezel, Santa Barbara, CA (US); Paul O'Brien, Melbourne (AU)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 13/934,987

(22) Filed: Jul. 3, 2013

(65) Prior Publication Data
US 2013/0296644 A1 Nov. 7, 2013

Related U.S. Application Data

(63) Continuation of application No. 13/049,453, filed on Mar. 16, 2011, now abandoned, which is a continuation-in-part of application No. 12/770,617, filed on Apr. 29, 2010.

(51) Int. Cl.
*A61F 5/00* (2006.01)
(52) U.S. Cl.
CPC ............... *A61F 5/0066* (2013.01); *A61F 5/005* (2013.01); *A61F 5/0056* (2013.01)
(58) Field of Classification Search
CPC ..... A61F 5/005; A61F 5/0053; A61F 5/0056; A61F 5/0059; A61F 5/0063
USPC ........ 600/37; 623/14.13, 23.64, 23.65, 23.68; 606/157
See application file for complete search history.

(56) References Cited

U.S. PATENT DOCUMENTS

| 1,174,814 A | 3/1916 | Brennan |
| 1,830,947 A | 11/1931 | Klingel |

(Continued)

FOREIGN PATENT DOCUMENTS

| CA | 949965 | 6/1974 |
| EP | 0230747 | 8/1987 |

(Continued)

OTHER PUBLICATIONS

Acuna-Goycolea et al.; 'Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus'; The Journal of Neuroscience; V. 25(32); pp. 7406-7419; Aug. 10, 2005.

(Continued)

*Primary Examiner* — Samuel Gilbert
(74) *Attorney, Agent, or Firm* — Gordon & Jacobson, P.C.

(57) ABSTRACT

In some embodiments, the present invention generally provides self-adjusting gastric banding systems for the treatment of obesity and obesity related conditions, as well as systems for allowing the automatic self-adjustment of gastric bands when a patient swallows a large bolus. In some embodiments, the present invention generally provides for gastric banding systems having a satiety booster, for example, to increase satiety levels when a patient desires to curb appetite at a particular time. In some embodiments, the present invention may provide for gastric banding systems that allow for both the automatic self-adjustment of gastric bands when a patient swallows a large bolus and an incorporated satiety booster for increasing satiety levels when a patient desires to curb appetite at a particular time.

15 Claims, 7 Drawing Sheets

(56) References Cited

U.S. PATENT DOCUMENTS

| | | |
|---|---|---|
| 1,999,683 A | 4/1935 | Borresen |
| 2,163,048 A | 6/1939 | McKee |
| 2,339,138 A | 1/1944 | Black |
| 2,405,667 A | 8/1946 | Andrew |
| 2,438,231 A | 3/1948 | Schultz |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |
| 4,399,809 A | 8/1983 | Baro |
| 4,408,597 A | 10/1983 | Tenney |
| 4,417,567 A | 11/1983 | Trick |
| 4,424,208 A | 1/1984 | Wallace |
| 4,442,153 A | 4/1984 | Meltsch |
| 4,450,375 A | 5/1984 | Siegal |
| 4,485,805 A | 12/1984 | Foster |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen |
| 4,582,640 A | 4/1986 | Smestad |
| 4,582,865 A | 4/1986 | Balazs |
| 4,592,339 A | 6/1986 | Kuzmak |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner |
| 4,696,288 A | 9/1987 | Kuzmak |
| 4,708,140 A | 11/1987 | Baron |
| 4,716,154 A | 12/1987 | Maelson |
| 4,753,086 A | 6/1988 | Schmidt |
| 4,760,837 A | 8/1988 | Petit |
| 4,803,075 A | 2/1989 | Wallace |
| 4,881,939 A | 11/1989 | Newman |
| 4,883,467 A | 11/1989 | Franetzki |
| 4,886,787 A | 12/1989 | De |
| 4,896,787 A | 1/1990 | Delamour |
| 4,915,690 A | 4/1990 | Cone |
| 4,925,446 A | 5/1990 | Garay |
| 4,944,487 A | 7/1990 | Holtermann |
| 4,944,659 A | 7/1990 | Labbe |
| 4,958,791 A | 9/1990 | Nakamura |
| 4,969,899 A | 11/1990 | Cox |
| 4,994,019 A | 2/1991 | Fernandez |
| 5,045,060 A | 9/1991 | Melsky |
| 5,074,868 A | 12/1991 | Kuzmak |
| 5,084,061 A | 1/1992 | Gau |
| 5,091,171 A | 2/1992 | Yu |
| 5,116,652 A | 5/1992 | Alzner |
| 5,120,313 A | 6/1992 | Elftman |
| 5,143,724 A | 9/1992 | Leshchiner |
| 5,152,770 A | 10/1992 | Bengmark |
| 5,160,338 A | 11/1992 | Vincent |
| 5,188,609 A | 2/1993 | Bayless |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner |
| 5,259,399 A | 11/1993 | Brown |
| 5,326,349 A | 7/1994 | Baraff |
| 5,343,894 A | 9/1994 | Frisch |
| 5,356,883 A | 10/1994 | Kuo et al. |
| 5,360,445 A | 11/1994 | Goldowsky |
| 5,391,156 A | 2/1995 | Hildwein |
| 5,399,351 A | 3/1995 | Leshchiner |
| 5,449,363 A | 9/1995 | Brust |
| 5,449,368 A | 9/1995 | Kuzmak |
| 5,458,568 A | 10/1995 | Racchini |
| 5,509,888 A | 4/1996 | Miller |
| 5,531,716 A | 7/1996 | Luzio |
| 5,535,752 A | 7/1996 | Halperin |
| 5,554,113 A | 9/1996 | Novak |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Ågerup |
| 5,653,718 A | 8/1997 | Yoon |
| 5,658,298 A | 8/1997 | Vincent |
| 5,676,162 A | 10/1997 | Larson |
| 5,695,504 A | 12/1997 | Gifford |
| 5,704,893 A | 1/1998 | Timm |
| 5,713,911 A | 2/1998 | Racenet |
| 5,733,257 A | 3/1998 | Sternby |
| 5,748,200 A | 5/1998 | Funahashi |
| 5,766,232 A | 6/1998 | Grevious |
| 5,769,877 A | 6/1998 | Barreras |
| 5,785,295 A | 7/1998 | Tsai |
| 5,817,113 A | 10/1998 | Gifford |
| 5,827,529 A | 10/1998 | Ono |
| 5,833,698 A | 11/1998 | Hinchliffe |
| 5,861,014 A | 1/1999 | Familoni |
| RE36,176 E | 3/1999 | Kuzmak |
| 5,886,042 A | 3/1999 | Yu |
| 5,904,697 A | 5/1999 | Gifford |
| 5,910,149 A | 6/1999 | Kuzmak |
| 5,928,195 A | 7/1999 | Malamud |
| 5,938,669 A | 8/1999 | Klaiber |
| 5,944,696 A | 8/1999 | Bayless |
| 5,944,751 A | 8/1999 | Laub |
| 5,993,473 A | 11/1999 | Chan |
| 6,013,679 A | 1/2000 | Kuo |
| 6,024,340 A | 2/2000 | Lazarus |
| 6,024,704 A | 2/2000 | Meador |
| 6,048,309 A | 4/2000 | Flom |
| 6,067,991 A | 5/2000 | Forsell |
| 6,074,341 A | 6/2000 | Anderson |
| 6,074,378 A | 6/2000 | Mouri |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson |
| 6,171,321 B1 | 1/2001 | Gifford |
| 6,193,734 B1 | 2/2001 | Bolduc |
| 6,203,523 B1 | 3/2001 | Haller |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo |
| 6,306,088 B1 | 10/2001 | Krausman |
| 6,327,503 B1 | 12/2001 | Familoni |
| 6,371,965 B2 | 4/2002 | Gifford |
| 6,372,494 B1 | 4/2002 | Naughton |
| 6,383,218 B1 | 5/2002 | Sourdile |
| 6,383,219 B1 | 5/2002 | Telandro |
| 6,387,105 B1 | 5/2002 | Gifford |
| 6,417,750 B1 | 7/2002 | Sohn |
| 6,418,934 B1 | 7/2002 | Chin |
| 6,419,696 B1 | 7/2002 | Ortiz |
| 6,432,040 B1* | 8/2002 | Meah ............................. 600/37 |
| 6,439,539 B1 | 8/2002 | Powell |
| 6,443,957 B1 | 9/2002 | Addis |
| 6,443,965 B1 | 9/2002 | Gifford |
| 6,450,173 B1 | 9/2002 | Forsell |
| 6,450,946 B1 | 9/2002 | Forsell |
| 6,451,034 B1 | 9/2002 | Gifford |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |

(56) References Cited

U.S. PATENT DOCUMENTS

| | | |
|---|---|---|
| 6,454,785 B2 | 9/2002 | De Hoyos Garza |
| 6,457,801 B1 | 10/2002 | Fish |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker |
| 6,491,704 B2 | 12/2002 | Gifford |
| 6,491,705 B2 | 12/2002 | Gifford |
| 6,511,490 B2 | 1/2003 | Robert |
| 6,517,556 B1 | 2/2003 | Monassevitch |
| 6,527,701 B1 | 3/2003 | Sayet |
| 6,547,801 B1 | 4/2003 | Dargent |
| 6,565,582 B2 | 5/2003 | Gifford |
| 6,579,301 B1 | 6/2003 | Bales |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder |
| 6,646,628 B2 | 11/2003 | Shirochi |
| 6,676,674 B1 | 1/2004 | Dudai |
| 6,685,668 B1 | 2/2004 | Cho |
| 6,685,963 B1 | 2/2004 | Taupin |
| 6,691,047 B1 | 2/2004 | Fredericks |
| 6,715,731 B1 | 4/2004 | Post |
| 6,729,600 B2 | 5/2004 | Mattes |
| 6,754,527 B2 | 6/2004 | Stroebel |
| 6,767,924 B2 | 7/2004 | Yu |
| 6,811,136 B2 | 11/2004 | Eberhardt |
| 6,820,651 B2 | 11/2004 | Seuret |
| 6,834,201 B2 | 12/2004 | Gillies |
| 6,871,090 B1 | 3/2005 | He |
| 6,889,086 B2 | 5/2005 | Mass |
| 6,916,326 B2 | 7/2005 | Benchetrit |
| 6,921,819 B2 | 7/2005 | Piron |
| 6,924,273 B2 | 8/2005 | Pierce |
| 6,940,467 B2 | 9/2005 | Fischer |
| 6,966,875 B1 | 11/2005 | Longobardi |
| 7,017,583 B2 | 3/2006 | Forsell |
| 7,021,147 B1 | 4/2006 | Subramanian |
| 7,037,344 B2 | 5/2006 | Kagan |
| 7,040,349 B2 | 5/2006 | Moler |
| 7,054,690 B2 | 5/2006 | Imran |
| 7,058,434 B2 | 6/2006 | Wang |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis |
| 7,128,750 B1 | 10/2006 | Stergiopulos |
| 7,144,400 B2 | 12/2006 | Byrum |
| 7,172,607 B2 | 2/2007 | Hoefle |
| 7,177,693 B2 | 2/2007 | Starkebaum |
| 7,191,007 B2 | 3/2007 | Desai |
| 7,204,821 B1 | 4/2007 | Clare |
| 7,223,239 B2 | 5/2007 | Schulze |
| 7,238,191 B2 | 7/2007 | Bachmann |
| 7,240,607 B2 | 7/2007 | Fish |
| 7,255,675 B2 | 8/2007 | Gertner |
| 7,263,405 B2 | 8/2007 | Boveja |
| 7,282,023 B2 | 10/2007 | Frering |
| 7,288,064 B2 | 10/2007 | Boustani |
| 7,297,103 B2 | 11/2007 | Jarsaillon |
| 7,299,082 B2 | 11/2007 | Feldman |
| 7,310,557 B2 | 12/2007 | Maschino |
| 7,311,716 B2 | 12/2007 | Byrum |
| 7,311,717 B2 | 12/2007 | Egle |
| 7,314,443 B2 | 1/2008 | Jordan |
| 7,314,636 B2 | 1/2008 | Caseres |
| 7,338,433 B2 | 3/2008 | Coe |
| 7,340,306 B2 | 3/2008 | Barrett |
| 7,351,198 B2 | 4/2008 | Byrum |
| 7,351,240 B2 | 4/2008 | Hassler |
| 7,364,542 B2 | 4/2008 | Jambor |
| 7,367,340 B2 | 5/2008 | Nelson |
| 7,367,937 B2 | 5/2008 | Jambor |
| 7,374,565 B2 | 5/2008 | Hassler |
| 7,390,294 B2 | 6/2008 | Hassler |
| 7,396,353 B2 | 7/2008 | Lorenzen |
| 7,416,528 B2 | 8/2008 | Crawford |
| 7,457,668 B2 | 11/2008 | Cancel |
| 7,481,763 B2 | 1/2009 | Hassler |
| 7,500,944 B2 | 3/2009 | Byrum |
| 7,502,649 B2 | 3/2009 | Ben-Haim |
| 7,530,943 B2 | 5/2009 | Lechner |
| 7,594,885 B2 | 9/2009 | Byrum |
| 7,599,743 B2 | 10/2009 | Hassler |
| 7,599,744 B2 | 10/2009 | Giordano |
| 7,601,162 B2 | 10/2009 | Hassler |
| 7,615,001 B2 | 11/2009 | Jambor |
| 7,618,365 B2 | 11/2009 | Jambor |
| 7,658,196 B2 | 2/2010 | Ferreri |
| 7,670,279 B2 | 3/2010 | Gertner |
| 7,699,770 B2 | 4/2010 | Hassler |
| 7,712,470 B2 | 5/2010 | Gertner |
| 7,727,141 B2 | 6/2010 | Hassler |
| 7,741,476 B2 | 6/2010 | Lebreton |
| 7,758,493 B2 | 7/2010 | Gingras |
| 7,763,039 B2 | 7/2010 | Ortiz |
| 7,766,815 B2 | 8/2010 | Ortiz |
| 7,771,439 B2 | 8/2010 | Griffiths |
| 7,775,215 B2 | 8/2010 | Hassler |
| 7,775,966 B2 | 8/2010 | Dlugos |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos |
| 7,862,502 B2 | 1/2011 | Pool |
| 7,879,068 B2 | 2/2011 | Dlugos |
| 7,951,067 B2 | 5/2011 | Byrum |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner |
| 2003/0066536 A1 | 4/2003 | Forsell |
| 2003/0073880 A1 | 4/2003 | Polsky |
| 2003/0093157 A1 | 5/2003 | Casares |
| 2003/0100910 A1 | 5/2003 | Gifford |
| 2003/0120288 A1 | 6/2003 | Benchetrit |
| 2003/0148995 A1 | 8/2003 | Piron |
| 2003/0158564 A1 | 8/2003 | Benchetrit |
| 2003/0158569 A1 | 8/2003 | Wazne |
| 2003/0181890 A1 | 9/2003 | Schulze |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker |
| 2004/0064110 A1 | 4/2004 | Forsell |
| 2004/0068847 A1 | 4/2004 | Belisle |
| 2004/0106899 A1 | 6/2004 | McMichael |
| 2004/0133219 A1 | 7/2004 | Forsell |
| 2004/0147816 A1 | 7/2004 | Policker |
| 2004/0148034 A1 | 7/2004 | Kagan |
| 2004/0153106 A1 | 8/2004 | Dudai |

(56) References Cited

U.S. PATENT DOCUMENTS

| | | |
|---|---|---|
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon |
| 2004/0254537 A1 | 12/2004 | Conlon |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0002984 A1 | 1/2005 | Byrum |
| 2005/0038484 A1 | 2/2005 | Knudson |
| 2005/0038498 A1 | 2/2005 | Dubrow |
| 2005/0055039 A1 | 3/2005 | Burnett |
| 2005/0070934 A1 | 3/2005 | Tanaka |
| 2005/0070937 A1* | 3/2005 | Jambor et al. ................ 606/153 |
| 2005/0082793 A1 | 4/2005 | Lee |
| 2005/0100779 A1 | 5/2005 | Gertner |
| 2005/0104457 A1 | 5/2005 | Jordan |
| 2005/0119672 A1 | 6/2005 | Benchetrit |
| 2005/0119674 A1 | 6/2005 | Gingras |
| 2005/0131383 A1 | 6/2005 | Chen |
| 2005/0131485 A1 | 6/2005 | Knudson |
| 2005/0136122 A1 | 6/2005 | Sadozai |
| 2005/0142152 A1 | 6/2005 | Leshchiner |
| 2005/0143765 A1 | 6/2005 | Bachmann |
| 2005/0143766 A1 | 6/2005 | Bachmann |
| 2005/0154274 A1 | 7/2005 | Jarsaillon |
| 2005/0171568 A1 | 8/2005 | Duffy |
| 2005/0183730 A1 | 8/2005 | Byrum |
| 2005/0192531 A1* | 9/2005 | Birk ........................... 604/96.01 |
| 2005/0192601 A1 | 9/2005 | Demarais |
| 2005/0192629 A1 | 9/2005 | Saadat |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler |
| 2005/0267533 A1 | 12/2005 | Gertner |
| 2005/0271729 A1 | 12/2005 | Wang |
| 2005/0277899 A1 | 12/2005 | Conlon |
| 2005/0283041 A1 | 12/2005 | Egle |
| 2005/0288739 A1 | 12/2005 | Hassler |
| 2005/0288740 A1 | 12/2005 | Hassler |
| 2006/0015138 A1 | 1/2006 | Gertner |
| 2006/0020298 A1 | 1/2006 | Camilleri |
| 2006/0041183 A1 | 2/2006 | Massen |
| 2006/0074439 A1 | 4/2006 | Garner |
| 2006/0074473 A1 | 4/2006 | Gertner |
| 2006/0089571 A1 | 4/2006 | Gertner |
| 2006/0122147 A1 | 6/2006 | Wohlrab |
| 2006/0127246 A1* | 6/2006 | Forsell ........................ 417/412 |
| 2006/0142700 A1 | 6/2006 | Sobelman |
| 2006/0142790 A1 | 6/2006 | Gertner |
| 2006/0161139 A1 | 7/2006 | Levine |
| 2006/0161186 A1 | 7/2006 | Hassler |
| 2006/0167531 A1 | 7/2006 | Gertner |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212051 A1 | 9/2006 | Snyder |
| 2006/0212053 A1 | 9/2006 | Gertner |
| 2006/0229696 A1 | 10/2006 | Boustani |
| 2006/0235448 A1 | 10/2006 | Roslin |
| 2006/0246137 A1 | 11/2006 | Hermitte |
| 2006/0247721 A1 | 11/2006 | Maschino |
| 2006/0247722 A1 | 11/2006 | Maschino |
| 2006/0252982 A1 | 11/2006 | Hassler |
| 2006/0252983 A1 | 11/2006 | Lembo |
| 2006/0257488 A1 | 11/2006 | Hubbard |
| 2006/0264699 A1 | 11/2006 | Gertner |
| 2006/0276812 A1 | 12/2006 | Hill |
| 2006/0293627 A1 | 12/2006 | Byrum |
| 2007/0015954 A1 | 1/2007 | Dlugos |
| 2007/0015955 A1 | 1/2007 | Tsonton |
| 2007/0015956 A1 | 1/2007 | Crawford |
| 2007/0016231 A1 | 1/2007 | Jambor |
| 2007/0016262 A1 | 1/2007 | Gross |
| 2007/0027356 A1 | 2/2007 | Ortiz |
| 2007/0027358 A1 | 2/2007 | Gertner |
| 2007/0044655 A1 | 3/2007 | Fish |
| 2007/0077292 A1 | 4/2007 | Pinsky |
| 2007/0078476 A1 | 4/2007 | Hull |
| 2007/0125826 A1 | 6/2007 | Shelton |
| 2007/0156013 A1* | 7/2007 | Birk ............................. 600/37 |
| 2007/0167672 A1 | 7/2007 | Dlugos |
| 2007/0167982 A1 | 7/2007 | Gertner |
| 2007/0173685 A1 | 7/2007 | Jambor |
| 2007/0173888 A1 | 7/2007 | Gertner |
| 2007/0179335 A1 | 8/2007 | Gertner |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann |
| 2007/0250086 A1 | 10/2007 | Wiley |
| 2007/0255335 A1 | 11/2007 | Herbert |
| 2007/0255336 A1 | 11/2007 | Herbert |
| 2007/0265598 A1 | 11/2007 | Karasik |
| 2007/0265645 A1 | 11/2007 | Birk |
| 2007/0265646 A1 | 11/2007 | McCoy |
| 2007/0293716 A1 | 12/2007 | Baker |
| 2007/0298005 A1 | 12/2007 | Thibault |
| 2008/0009680 A1 | 1/2008 | Hassler |
| 2008/0015406 A1 | 1/2008 | Dlugos |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang |
| 2008/0108862 A1 | 5/2008 | Jordan |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool |
| 2008/0188766 A1 | 8/2008 | Gertner |
| 2008/0195092 A1 | 8/2008 | Kim |
| 2008/0208240 A1 | 8/2008 | Paz |
| 2008/0221598 A1 | 9/2008 | Dlugos |
| 2008/0243071 A1 | 10/2008 | Quijano |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |

(56) References Cited

U.S. PATENT DOCUMENTS

| | | |
|---|---|---|
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton |
| 2008/0287974 A1 | 11/2008 | Widenhouse |
| 2008/0287976 A1 | 11/2008 | Weaner |
| 2008/0300618 A1 | 12/2008 | Gertner |
| 2008/0319435 A1 | 12/2008 | Rioux |
| 2009/0054914 A1 | 2/2009 | Lechner |
| 2009/0062825 A1 | 3/2009 | Pool |
| 2009/0062826 A1* | 3/2009 | Steffen .................. 606/157 |
| 2009/0082793 A1 | 3/2009 | Birk |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0187202 A1 | 7/2009 | Ortiz |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1* | 8/2009 | Coe et al. .................. 606/157 |
| 2009/0216256 A1 | 8/2009 | Nicholson |
| 2009/0220176 A1 | 9/2009 | Fusco |
| 2009/0222031 A1 | 9/2009 | Axelsson |
| 2009/0222065 A1 | 9/2009 | Dlugos |
| 2009/0228063 A1 | 9/2009 | Dlugos |
| 2009/0228072 A1 | 9/2009 | Coe |
| 2009/0240100 A1 | 9/2009 | Forsell |
| 2009/0270904 A1 | 10/2009 | Birk et al. |
| 2009/0306462 A1 | 12/2009 | Lechner |
| 2010/0010291 A1 | 1/2010 | Birk |
| 2010/0049224 A1 | 2/2010 | Vargas |
| 2010/0087843 A1 | 4/2010 | Bertolote |
| 2010/0099945 A1 | 4/2010 | Birk |
| 2010/0100079 A1 | 4/2010 | Berkcan |
| 2010/0770617 | 4/2010 | Snow |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk |
| 2010/0191265 A1 | 7/2010 | Lau |
| 2010/0191271 A1 | 7/2010 | Lau |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk |
| 2010/0312046 A1 | 12/2010 | Lau |
| 2010/0312147 A1 | 12/2010 | Gertner |
| 2010/0324358 A1 | 12/2010 | Birk |
| 2010/0324359 A1 | 12/2010 | Birk |
| 2011/0071341 A1 | 3/2011 | Dlugos |
| 2011/0201874 A1 | 8/2011 | Birk |

FOREIGN PATENT DOCUMENTS

| | | |
|---|---|---|
| EP | 0416250 | 3/1991 |
| EP | 0611561 | 8/1994 |
| EP | 1036545 A2 | 9/2000 |
| EP | 1072282 | 1/2001 |
| EP | 1105073 | 6/2001 |
| EP | 1491167 | 12/2004 |
| EP | 1491168 | 12/2004 |
| EP | 1529502 | 5/2005 |
| EP | 1547549 A2 | 6/2005 |
| EP | 1574189 | 9/2005 |
| EP | 1600183 A1 | 11/2005 |
| EP | 1602346 A1 | 12/2005 |
| EP | 1704833 A2 | 9/2006 |
| EP | 1719480 A2 | 11/2006 |
| EP | 1736123 A1 | 12/2006 |
| EP | 1736195 | 12/2006 |
| EP | 1736202 | 12/2006 |
| EP | 1743605 A1 | 1/2007 |
| EP | 1829504 | 9/2007 |
| EP | 1829505 | 9/2007 |
| EP | 1829506 | 9/2007 |
| EP | 1967168 A2 | 9/2008 |
| EP | 1992315 | 11/2008 |
| EP | 2074970 A1 | 7/2009 |
| EP | 2074971 A1 | 7/2009 |
| EP | 2074972 A2 | 7/2009 |
| EP | 2095796 A1 | 9/2009 |
| EP | 2095798 | 9/2009 |
| EP | 2191796 | 6/2010 |
| FR | 2688693 | 9/1993 |
| FR | 2769491 | 4/1999 |
| FR | 2799118 | 4/2001 |
| GB | 1174814 A | 12/1969 |
| GB | 2090747 | 7/1982 |
| JP | 57171676 | 10/1982 |
| JP | 2019147 | 1/1990 |
| JP | 11244395 | 9/1999 |
| JP | 2003526410 | 9/2003 |
| JP | 2005131380 | 5/2005 |
| WO | 8600079 | 1/1986 |
| WO | 8600912 | 2/1986 |
| WO | 8911701 | 11/1989 |
| WO | 9000369 | 1/1990 |
| WO | 9220349 | 11/1992 |
| WO | 9402517 | 2/1994 |
| WO | 9633751 | 1/1996 |
| WO | 9835639 | 8/1998 |
| WO | 9835640 | 8/1998 |
| WO | 0000108 A1 | 1/2000 |
| WO | 0001428 | 1/2000 |
| WO | 0009047 A1 | 2/2000 |
| WO | 0009049 | 2/2000 |
| WO | 0015158 A1 | 3/2000 |
| WO | 0066196 | 11/2000 |
| WO | 0110359 A1 | 2/2001 |
| WO | 0112078 A1 | 2/2001 |
| WO | 0141671 | 6/2001 |
| WO | 0147435 | 7/2001 |
| WO | 0147575 A2 | 7/2001 |
| WO | 0149245 A2 | 7/2001 |
| WO | 0152777 | 7/2001 |
| WO | 0168007 | 9/2001 |
| WO | 0185071 | 11/2001 |
| WO | 0205753 | 1/2002 |
| WO | 0209792 | 2/2002 |
| WO | 0219953 | 3/2002 |
| WO | 0226317 | 4/2002 |
| WO | 02053093 | 7/2002 |
| WO | 02065948 | 8/2002 |
| WO | 02096326 | 12/2002 |
| WO | 03007782 | 1/2003 |
| WO | 03055420 | 7/2003 |
| WO | 03057092 | 7/2003 |
| WO | 03059215 | 7/2003 |
| WO | 03077191 | 9/2003 |
| WO | 03101352 A1 | 12/2003 |
| WO | 03105732 A1 | 12/2003 |
| WO | 2004014245 A1 | 2/2004 |
| WO | 2004019671 A2 | 3/2004 |
| WO | 2004108025 | 12/2004 |
| WO | 2004112563 A2 | 12/2004 |

(56) References Cited

FOREIGN PATENT DOCUMENTS

| WO | 2005007232 | | 1/2005 |
|---|---|---|---|
| WO | 2005009305 | A1 | 2/2005 |
| WO | 2005067994 | | 7/2005 |
| WO | 2005072195 | | 8/2005 |
| WO | 2005087147 | | 9/2005 |
| WO | 2005094447 | | 10/2005 |
| WO | 2005112888 | | 12/2005 |
| WO | 2006040647 | | 4/2006 |
| WO | 2006049725 | | 5/2006 |
| WO | 2006083885 | | 8/2006 |
| WO | 2006108203 | A2 | 10/2006 |
| WO | 2007067206 | | 6/2007 |
| WO | 2007081304 | A2 | 7/2007 |
| WO | 2007106727 | A2 | 9/2007 |
| WO | 2007114905 | | 10/2007 |
| WO | 2007145638 | | 12/2007 |
| WO | 2008058028 | A2 | 5/2008 |
| WO | 2008063673 | A1 | 5/2008 |
| WO | 2008134755 | | 11/2008 |
| WO | 2009050709 | A2 | 4/2009 |
| WO | 2009132127 | A1 | 10/2009 |
| WO | 2009136126 | A2 | 11/2009 |
| WO | 2010042493 | A1 | 4/2010 |

OTHER PUBLICATIONS

Adrian et al.; 'Mechanism of Pancreatic Polypeptide Release in Man.' The Lancet; pp. 161-163; Jan. 22, 1977.

Anson; 'Shape Memory Alloys—Medical Applications,' Source: Materials World, vol. 7, No. 12, pp. 745-747, Dec. 1999.

Asakawa et al; 'Antagonism of Ghrelin Receptor Reduces Food Intake and Body Weight Gain in Mice'; Gut.; V.52; pp. 947-952; 2003.

Baggio et al. 'Biology of Integrins: GLP-1 and GIP'; Gastroenrology; V. 132; pp. 2131-2157; 2007.

Ballantyne; 'Peptide YY(1-36) and Peptide YY(3-36): Part I. Distribution, Release, and Actions'; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; 'Physiology'; V. 5; pp. 55-57, 210, 428, 540, 554, 579, 584, 591; 2004.

Bio Enterics Lap-Band Adjustable Gastric Banding System, Inamed Health, pub. Aug. 28, 2003, pp. 1-115.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Burdyga et al.; 'Cholecystokinin Regulates Expression of Y2 Receptors in Vagal Afferent Neurons Serving the Stomach'; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Corno et al.; 'A new implantable device for telemetric control of pulmonary blood flow'; New ideas; received Apr. 24, 2004; received in revised form Jul. 12, 2002; 10 pages.

Corno et al.; 'FlowWatchTM in clipped and inclipped position'; Interact Cardio Vasc Thorac Surg 2002; 1:46-49; Copyright@2002 The European Asociation for Cardio-thoracic Surgery; 1 page.

Cummings et al.; 'Plasma Ghrelin Levels After Diet-Induced Weight Loss or Gastric Bypass Surgery'; N. Engl J. Med; V. 346, No. 21; pp. 1623-1630; May 23, 2002.

Cummings; 'Gastrointestinal Regulation of Foot Intake'; The Food Journal of Clinical Investigation; V. 117, N. 1; pp. 13-23; Jan. 2007.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; 'Molecular Weight of Heparin Using 13C Nuclear Magnetic Resonance Spectroscopy' Journal of Pharmaceutical Science, V. 84,12; 1995, Abstract only.

Doldi et al.; 'Intragastric Balloon: Another Option for Treatment of Obesity and Morbid Obesity'; Hepato-Gastroenterology; V. 51, N. 55; pp. 294-307; Jan.-Feb. 2004.

Doldi et al.; 'Treatment of Morbid Obesity with Intragastric Balloon in Association with Diet'; Obesity Surgery; V. 10, pp. 583-587; 2000.

Ekblad et al.; 'Distribution of Pancreatic Peptide and Peptide-YY'; Peptides; V. 23; pp. 251-261;2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; 'The Incretins: From the concept to their use in the treatment of type 2 diabetes. Part A: IncretinsIncretinsIncretinsIncretinsIncretins: Concept and physiological functions'; Diabetes and Metabolism; V. 34; pp. 550-559; 2008.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al., 'Gut Hormones and Appetite Control', Oral Diseases, 2009, 15:18-26.

Hassan et al.; 'Effects of Adjuvants to Local Anesthetics on Their Duration III Experimental Studies of Hyaluronic Acid' Abstract Pub Med [Acta Anesthesiol Scand.; 29 (4): 384-8], 1 page; May 1985.

Hodson et al.; 'Management of Obesity with the New Intragastric Balloon'; Obesity Surgery; V. 11, pp. 327-329,2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; 'Gastrointestinal Factors in Hunger and Satiety'; Neurosci. and Behav. Rev.; V. 6; pp. 145-164; 1982.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; 'Exogenous Ghrelin Enhances Endocrine and Exocrine Regeneration in Pancreatectomized Rats'; J. Gastrointest Surg.; V. 13; pp. 775-783, 2009.

(56) References Cited

OTHER PUBLICATIONS

Kesty et al., 'Hormone-based Therapies in the Regulation of Fuel Metabolism and Body Weight', Expert Opin. Biol. Ther., 2008, 8(11): 1733-1747.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Kojima et al., 'A Role for Pancreatic Polypeptide in Feeding and Body Weight Regulation', Peptides, 2007, 28:459-463.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; 'Gut Hormone Profiles Following Bariatric Surgery Favor an Anorectic State, Facilitate Weight Loss, and Improve Metabolic Parameters'; Ann. Surg; V. 243; No. 1; pp. 108-114; Jan. 2006.
Liu et al.; 'Adjuvant Hormonal Treatment With Peptide YY or Its Analog Decreases Human Pancreatic Carcinoma Growth'; The American Journal of Surgery; V. 171; pp. 192-196; Jan. 1996.
Mathus-Vliegen et al. 'Intragastric Balloons for Morbid Obesity: Results, Patient Tolerance and Balloon Life Span'; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; 'Processing and metabolism of Peptide-YY: Pivotal roles of Dipeptidase-IV, Aminopeptidase-P, and Endopeptidase-24. 11'; Endocrinology; V. 134, No. 5; pp. 2088-2094;1994.
Naslund et al.; 'Prandial Subcutaneous Injection of Glucagon-Like Peptide'; Br. J. Nutr.; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; 'Pulmonary delivery of a GLP-1 receptor agonist, BMS-686117'; International Journal of Pharmaceutics; V. 366; pp. 218-220; 2008.
Rang et al.; 'Pharmacology'; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. 'Peptide YY: A Potential Therapy for Obesity'; Current Drug Targets; V. 6; pp. 171-179; 2005.
Sannino et al., 'Crosslinking of Cellulose Derivatives and Hyaluronic Acid with Water-Soluble Carbodiimide,' Polymer 46(2005)pp. 11206-11212.
Shechter et al.; "Reversible PEGylation of peptide YY3-36 prolongs its inhibition of food intake in mice"; FEBS Letters; V. 579; pp. 2439-2444; 2005.
Silver et al.; 'Physical Properties of Hyaluronic Acid and Hydroxypropylmethylcellulose in Solution: Evaluation of Coating Ability' Journal of Applied Biomaterials, V. 5; pp. 89-98, 1994.
Small et al.; 'Gut hormones and the control of appetite'; TRENDS in Endocrinology and Metabolism; V. 15; No. 6; pp. 259-263; Aug. 2004.
Stanley et al.; 'Gastrointestinal Satiety Signals III. Glucagon-like Peptide 1, oxyntomodulin, peptide YY, and pancreatic polypeptide'; Am. J. Physiol Gastrointest Liver Physiol; V. 286; pp. 693-697; 2004.
Tezel, 'The Science of Hyaluronic Acid Dermal Fillers,' Journal of Cosmetic and Laser Therapy (2008) 10: pp. 35-42.
Tolhurst et al.; 'Nutritional regulation of glucagon-like peptidel secretion'; J. Physiol.; V. 587, No. I;pp. 27-32; 2009.
Totte et al.; "Weight Reduction by Means of Intragastric Device: Experience with the Bioenterics Intragastric Balloon", Obesity Surgery; V. 11, pp. 519-523; 2001.
Tough et al.; 'Y4 Receptors Mediate the Inhibitory Responses of Pancreatic Polypeptide in Human and Mouse Colon Mucosa'; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wahlen et al.; 'The BioEnterics Intragastric Balloon (BIB): How to Use It'; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; 'Preparation of Extremely Obese Patients for Laparoscopic Gastric Banding by Gastric Balloon Therapy'; Obesity Surgery; V. 9, pp. 261-264, 1999.
Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.
Yuzuriha et al.; "Gastrointestinal Hormones (anorexigenic peptide YY and orexigenic ghrelin) influence neural tube development"; Faseb J.; V. 21; pp. 2108-2112; 2007.
Brown et al; 'Symmetrical Pouch Dilation After Laparoscopic Adjustable Gastric Banding: Incidence and Management'; Obesity Surgery; V. 18, pp. 1104-1108; 2008.
Ceelen et al.; 'Surgical Treatment of Severe Obesity With a Low-Pressure Adjustable Gastric Band: Experimental Data and Clinical Results in 625 Patients'; Annals of Surgery; V. 237, No. I;pp. 10-16; 2003.
Dixon et al.; 'Pregnancy After Lap-Band Surgery: Management of the Band to Achieve Healthy Weight Outcomes'; Obesity Surgery; V. 11, pp. 59-65; 2001.
Neary et al.; 'Peptide YY(3-36) and Glucagon-Like Peptide-1.sub. (7-36) Inhibit Food Intake Additively'; Endocrinology; V.146; pp. 5120-5127; 2005.
Padidela et al.; 'Elevated basal and post-feed glucagon-like petide 1 (GLP-1) concentrations in the neonatel period'; European Journal of Endocrinology; v. 160; pp. 53-58; 2009.
Shi et al; 'Sexually Dimorphic Responses to Fat Loss After Caloric Restriction or Surgical Lipectomy'; Am. J. Physiol. Endocrinol. Metab.; V. 293; E316-E326; 2007.
Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

* cited by examiner

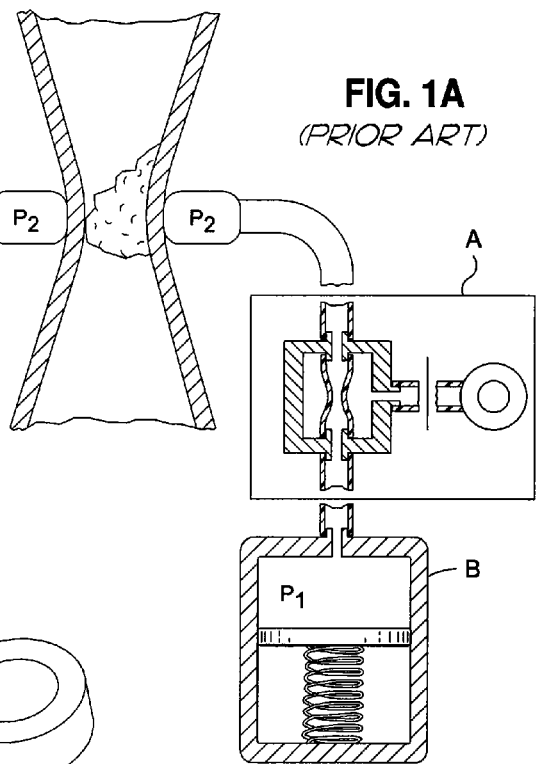
FIG. 1A
(PRIOR ART)
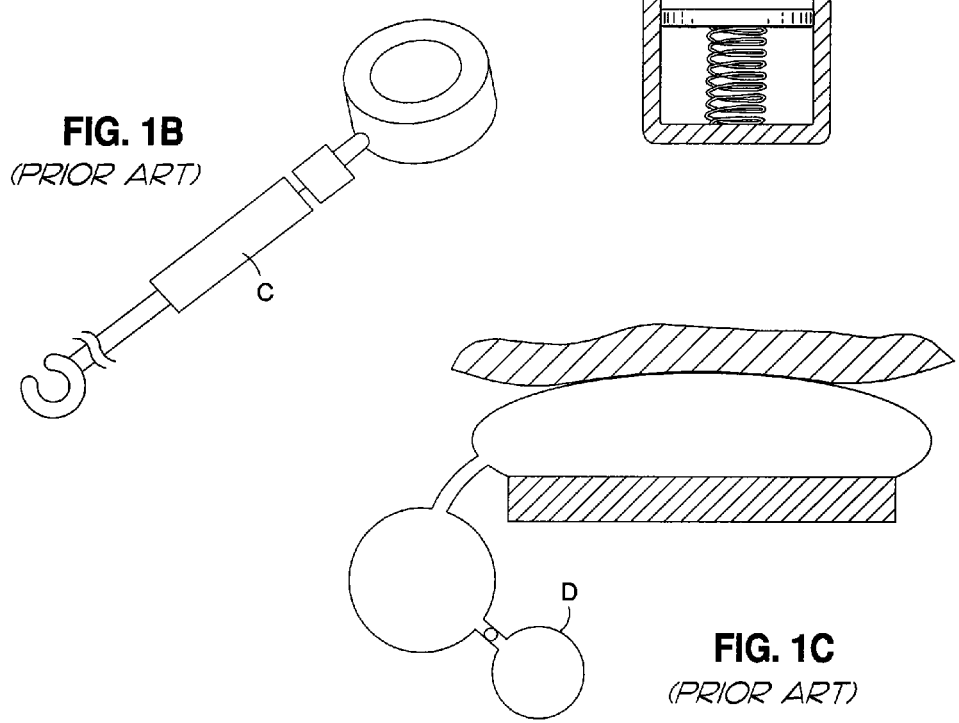
FIG. 1B
(PRIOR ART)
FIG. 1C
(PRIOR ART)

SELF-ADJUSTING GASTRIC BAND HAVING VARIOUS COMPLIANT COMPONENTS AND/OR A SATIETY BOOSTER

CROSS REFERENCE TO RELATED APPLICATIONS

This application is a continuation of U.S. patent application Ser. No. 13/049,453, filed Mar. 16, 2011, which is a continuation-in-part of U.S. patent application Ser. No. 12/770,617, filed on Apr. 29, 2010. The entire contents of which are hereby incorporated by reference herein.

FIELD

The present invention generally relates to medical systems and apparatus and uses thereof for treating obesity and/or obesity-related diseases, and more specifically, relates to gastric banding systems that self-adjust to changes in a patient and/or provides a satiety booster.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND APO (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Sometimes, adjustment of a gastric band may be desirable in between adjustments made by a physician. For example, during normal operation of the gastric band, the band applies pressure to the outer surface of the upper stomach. But in some instances, the patient may swallow a bolus that is too large to pass through the constriction produced by the band. The result can be a painful experience which, if it persists, may require medical intervention to release the blockage.

Some attempts have been made to account for this possibility of blockage. For example, with reference to FIG. 1A, Coe, et al., U.S. Patent Pub. No. 2009/0216255 discloses a flow control device A that moves fluid between a hydraulic restriction system and a fluid source B. The additional flow control device A controls a rate of fluid flow between the restriction device and the fluid source B. With reference to FIG. 1B, Coe, et al., European Patent Application No. 2 074 970 A1 discloses a separate restriction device and pressure adjustment device C. The pressure adjustment device C regulates a constant force applied by the restriction device using, for example, a bellows and a spring.

With reference to FIG. 1C, Lechner, U.S. Patent Pub. No. 2009/0054914 discloses a controllable stomach band that has a chamber for controlling restriction of the stomach band. The chamber is coupled to a separate pressure chamber D that receives fluid leaving the chamber in the stomach band. The pressure chamber D is separated from the esophageal-gastric junction of the patient's stomach.

With reference to FIG. 2, Forsell, U.S. Patent Pub. No. 2004/0064110 discloses an injection port E which can be pressed to change the volume in the gastric band.

With reference to FIG. 3, Steffen, U.S. Patent Pub. No. 2009/0062826 discloses an adjustable gastric band with a "conveyance device" that is powered by a "power storage device." The power storage device operates the conveyance device to move fluid between expandable chambers to adjust the gastric band.

Accordingly, in certain embodiments, it may be desirable to develop a self-adjusting gastric band that will provide the needed pressure to the stomach to create the stoma and facilitate weight control, but that will also adapt and open up to allow a large bolus to pass through. Additionally, it may be desirable to make the adjustments without additional, complicated fluid control mechanisms, flow rate limiting devices, and/or valves to regulate the transfer of fluid within the self-adjusting gastric band. Moreover, it is desirable to make these adjustments to the gastric band utilizing compliant components to both reduce and restore the constriction of the gastric band.

Accordingly, in certain embodiments, it is desirable to develop a gastric band having a bladder that a patient may press to obtain a satiety boost.

SUMMARY

Generally described herein are certain embodiments directed to automatic, self-adjusting, gastric banding systems that are capable of automatically relaxing and contracting in response to a large bolus passing through the area of a patient's stomach constricted by a gastric band. The apparatus and systems described herein in these certain embodiments aid in facilitating obesity control and/or treating obesity-related diseases while being non-invasive once implanted. Furthermore, certain embodiments of the self-adjusting gastric banding systems disclosed herein may be automatically adjustable without complicated fluid control mechanisms, flow rate limiting devices, and/or valves. The automatic adjustments may also be made in response to other changes in the patient's esophageal-gastric junction, for example, in response to size, shape, and/or location changes.

In one embodiment, a self-adjusting gastric band automatically adjusts to allow a large bolus of food to pass through a constriction in the patient's stomach formed by the gastric band. The gastric band comprises an inflatable portion that is disposable about an esophageal-gastric junction of the patient. The gastric band also comprises an access port fluidly coupled to the inflatable portion via tubing to fill and drain the inflatable portion.

Further, the gastric band comprises a first compliant portion coupled to a part of the system. For example, the first compliant portion may be coupled to the inflatable portion, the access port, and/or the tubing. The first compliant portion automatically relaxes the constriction formed by the self-adjusting gastric band and allows the large bolus to pass through the constriction. After the bolus passes through the constriction, the gastric band automatically returns to its previous state.

In accordance with various embodiments, the first compliant portion facilitates automatically relaxing the constriction formed by the self-adjusting gastric band without causing a fluid to exit the inflatable portion of the gastric band. For example, the self-adjusting gastric band may comprise a ring coupled to the inflatable portion of the gastric band. The ring provides structure and support to the inflatable portion, and the ring facilitates disposing the inflatable portion about the esophageal-gastric junction.

The ring may be a flexible ring with a diameter that expands when a predetermined pressure is generated in the inflatable portion. For example, the predetermined pressure may be generated in response to the large bolus passing through the esophageal-gastric junction. The flexible ring expands to automatically relax the constriction formed by the self-adjusting gastric band. In various embodiments, the ring has a durometer in the range of approximately 20 to approximately 70.

According to a further embodiment, the first compliant portion receives a first amount of fluid from the inflatable portion when the large bolus causes a pressure in the first compliant portion to exceed an expansion pressure. Receiving the first amount of fluid from the inflatable portion facilitates relaxing the constriction formed by the self-adjusting gastric band and allowing the large bolus to pass through the constriction.

In an embodiment, the first compliant portion is fluidly coupled to the inflatable portion. The first compliant portion facilitates removing the first amount of fluid from the inflatable portion when the large bolus passes through the constriction.

According to another embodiment, the self-adjusting gastric band further comprises a second compliant portion fluidly coupled to the access port. The second compliant portion automatically removes a second amount of fluid from the inflatable portion via the access port to facilitate relaxing the constriction formed by the inflatable portion.

The tubing of the gastric banding system may be compliant tubing that expands in response to a pressure in the tubing exceeding a tubing expansion pressure when the large bolus passes through the constriction formed by the self-adjusting gastric band. In this regard, a third amount of fluid is removed from the inflatable portion when the compliant tubing expands. The tubing may be perforated to facilitate receiving the fluid from the inflatable portion via the tubing.

Furthermore, another embodiment of the self-adjusting gastric band comprises a third compliant portion fluidly coupled to the tubing for automatically receiving a third amount of fluid from the inflatable portion via the tubing when the large bolus enters the esophageal-gastric junction. Receiving the third amount of fluid from the inflatable portion facilitates relaxing the constriction formed by the gastric band and allowing the large bolus to pass through the constriction.

The compliant components, according to various embodiments, comprise a kink-resisting feature. Further, the compliant components may comprise a leak-resisting feature. These components may be an elastic polymer, a balloon, a rubber container, a silicone container, a collapsible container, a bellows, and combinations thereof.

Generally described herein are certain embodiments directed to satiety boosting bladders which may transfer fluid from the bladder to inflatable portions of a gastric band, thereby tightening the gastric band and providing the patient a "satiety boost". After a period of time, the fluid may return from the gastric band back to the satiety boosting bladder.

In one embodiment, the satiety boosting bladder may be designed to allow for the free flow of fluids in and out of the gastric banding system without requiring valves and without the need to interface with an injection needle. The satiety boosting bladder may allow for intentional fluid transfer when the patient consciously presses on the bladder (by pressing on the skin area near the bladder).

In one embodiment, a gastric band system may include a satiety boosting bladder located in fluid connection between the gastric band and an access port. The satiety boosting bladder may be physically located beneath the skin of a patient but above the rectus muscle fascia such that the patient may induce pressure on the bladder and disperse fluid to the gastric band by pressing on the skin area closest to the location of the bladder.

In one embodiment, the satiety boosting bladder may be fluidly coupled to one end of an access port, wherein the access port may be located between the satiety boosting bladder and a tube coupling the access port to a gastric band.

In one embodiment, the satiety boosting bladder may be spherically shaped, rectangularly shaped, or circularly shaped. Additionally, and/or alternatively, the satiety boosting bladder may have non-uniform, tapered walls.

In one embodiment, the satiety boosting bladder may be a series of cylindrical components or a coiled component.

In one embodiment, the satiety boosting bladder may include flow restriction or flow controlling components such as a flow restrictor and/or a valve.

BRIEF DESCRIPTION OF THE DRAWINGS

FIG. 1A illustrates a prior art system that includes a flow rate limiting device.

FIG. 1B illustrates a prior art system that includes a fluid control mechanism.

FIG. 1C illustrates a prior art system that includes a valve and a chamber separated from the esophageal-gastric junction.

DETAILED DESCRIPTION

The present invention generally provides self-adjusting gastric banding systems, for example, for treatment of obesity and obesity related conditions, as well as systems for allowing automatic self-adjustment of gastric bands when a patient swallows a large bolus.

Self-adjusting gastric bands are effective in helping a patient lose weight when the band is properly tightened around the patient's esophageal-gastric junction. During normal operation, the gastric band applies pressure to the outer surface of the upper stomach. But, in some instances, the patient may swallow a bolus which is too large to pass through the constriction produced by the gastric band—for example, when the patient swallows a large piece of steak. The result can be a painful experience which, if it persists, may require medical intervention to release the blockage.

In accordance with various embodiments of the present invention, the self-adjusting gastric band provides the needed pressure to the stomach to encourage weight loss. However, when a large bolus of food is swallowed, the self-adjusting gastric band temporarily and automatically opens up to allow the bolus through. After the bolus passes through, the mechanisms within the gastric band return the gastric band to its original size and shape. In an embodiment, electrical power and/or power external to the patient is not utilized to perform these adjustments. Further, in an embodiment, complicated fluid control mechanisms, flow rate limiting devices, and/or valves are not utilized to regulate the transfer of fluid within the self-adjusting gastric band.

Figure 2:
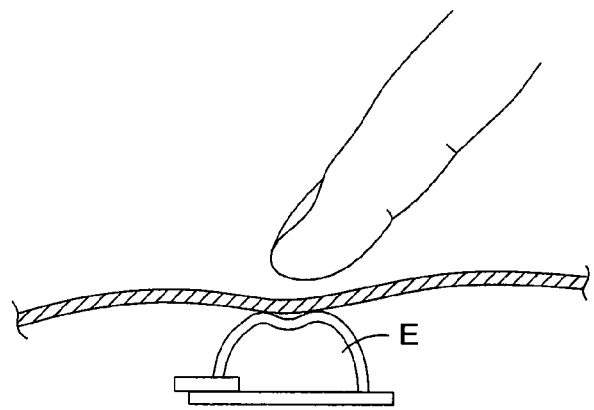
FIG. 2 illustrates a prior art system with a pressable injection port.
Figure 3:
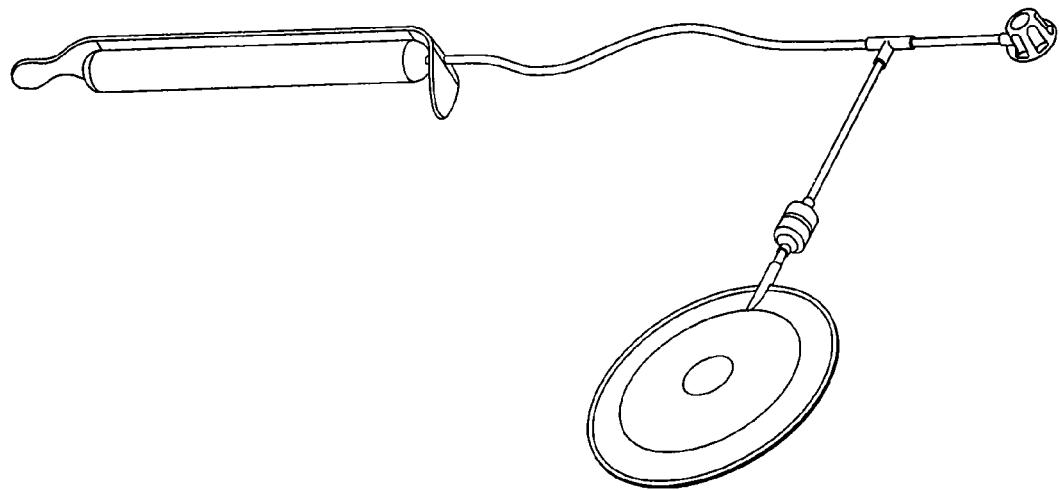
FIG. 3 illustrates a prior art system with a gastric banding system that is immune to deliberate influence by a patient.
Figure 4:
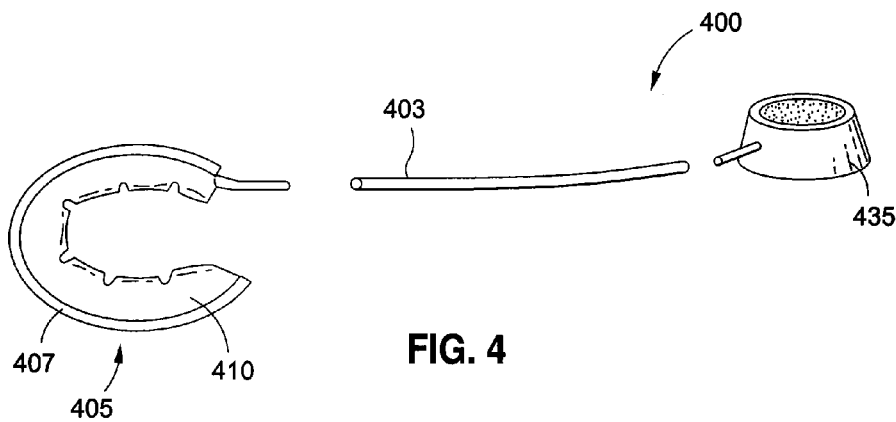
FIG. 4 illustrates an exploded, perspective view of a self-adjusting gastric banding system according to an embodiment of the present invention.

Turning now to FIG. 4, a self-adjusting gastric banding system 400 comprises a gastric band 405 coupled to a subcutaneous injection port 435 via tubing 403. The gastric band 405 comprises a circular ring 407 and an inflatable portion 410 disposed on the inside of the ring 407. The inflatable portion 410 separates the patient's stomach from the ring 407 when the gastric band 405 is implanted around the esophageal-gastric junction of the patient's stomach. The ring 407 provides structure and support to the inflatable portion 410, and facilitates implanting the gastric band 405 around the patient's stomach.

The access port 435 may be sutured onto the rectus muscle sheath or any other conveniently accessible muscle. The rectus muscle sheath provides a secure surface on which to attach the access port 435 under a layer of fat that separates the patient's skin from the muscle.

The inflatable portion 410 may be filled and drained with a fluid via the tubing 403. For example, the tubing 403 may be connected to the subcutaneous access port 435 for filling and draining the inflatable portion 410 via subcutaneous injections. The inflatable portion 410 may also be coupled to a reservoir to facilitate automatic adjustment of the inflatable portion 410, and the constriction it causes, when a large bolus attempts to pass through the constriction. When more fluid is introduced in the inflatable portion 410, the constriction around the stomach generally becomes tighter. Correspondingly, when less fluid is present, the constriction loosens and/or opens up.

The fluids used within the gastric band 405 may include any fluid that is biocompatible and incompressible. The fluid has no adverse effect on the patient in the unlikely event that a leak emanates from the system. The fluid can simply be water or any biocompatible polymer oil such as caster oil. In an example embodiment, the fluid is saline, a drug, and/or combinations thereof.

In an embodiment, the ring 407 is designed to be a compliant portion of the gastric band 405. For example, the ring 407 may flex and/or expand in response to a bolus of food moving through the constriction caused by the gastric band 405. The ring 407 may have flexible components and rigid components, such that the flexible components expand when a certain elevated and/or maximum pressure is reached in the inflatable portion 410. This elevated pressure may exist due to the presence of an obstruction such as a bolus near the gastric band 405. As the ring 407 expands, the diameters of the ring 407 and the inflatable portion 410 increase, and the constriction on the stomach due to the gastric band 405 is reduced to allow the bolus to pass through. When the bolus has passed, the elevated pressure no longer exists, and the gastric band 405 returns to the pre-obstruction state.

In another embodiment, the entire ring 407 may be flexible and/or expandable such that a diameter of the ring 407 increases in response to the elevated pressure in the inflatable portion 410. For example, the ring 407 may be constructed of silicone that has a durometer in the range of approximately 20 to approximately 70.

It should be understood that the flexible ring 407 and the other mechanisms disclosed herein for automatically adjusting the constriction of the gastric band 405 are only example embodiments. Any mechanism for automatically adjusting the constriction of the gastric band 405 that does not include electrical power, power external to the patient, complicated fluid control mechanisms, flow rate limiting devices, and/or valves is contemplated within the scope of the present invention.

Furthermore, although various compliant components are illustrated in each of the figures, it should be understood that any combination of the various compliant components may be utilized in different embodiments. For example, an embodiment may include one compliant component—only the ring, the tubing, or the access port may be compliant. In other embodiments, any combination of the ring, the tubing, and the access port may be compliant. For example, an embodiment may include a compliant ring and a compliant port, an embodiment may include compliant tubing and a compliant port, or an embodiment may include a compliant ring and compliant tubing. Any combination of compliant components is contemplated within the scope of the present invention.

Figure 5:
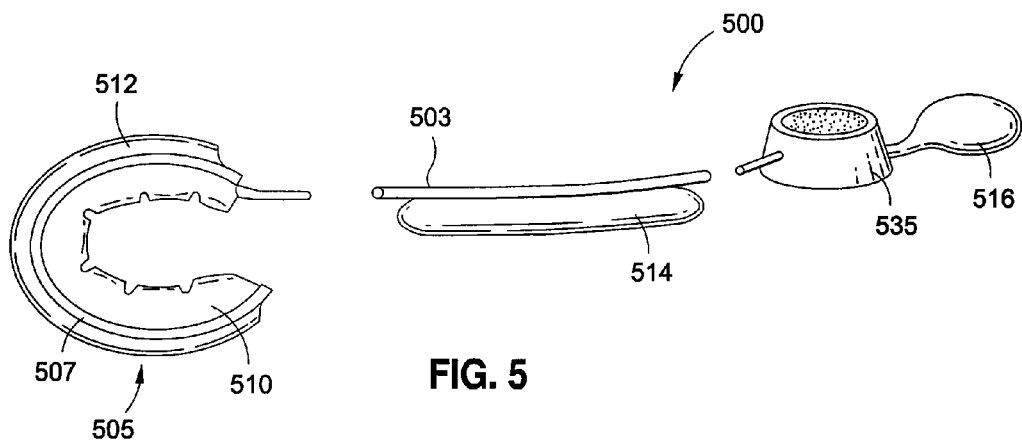
FIG. 5 illustrates an exploded, perspective view of a self-adjusting gastric banding system having various compliant components according to an embodiment of the present invention.

With reference to FIG. 5, various compliant components may be utilized to automatically adjust the constriction of the gastric band 505 about the esophageal-gastric junction of the patient's stomach. Although three compliant components are illustrated in FIG. 5, as noted above, one or more of the components may be present in various embodiments of the present invention.

For example, in an embodiment, a band compliant component 512 is fluidly coupled to the inflatable portion 510 of the gastric band 505. The compliant component 512 is located on the outside of the ring 507, opposite the inflatable portion, and may be coupled to the ring 507 and the inflatable portion. Further, in an embodiment, one or more fluid ports may extend from the inflatable portion 510 to the compliant component 512 to fluidly couple the inflatable portion 510 to the compliant component 512.

Figure 6:
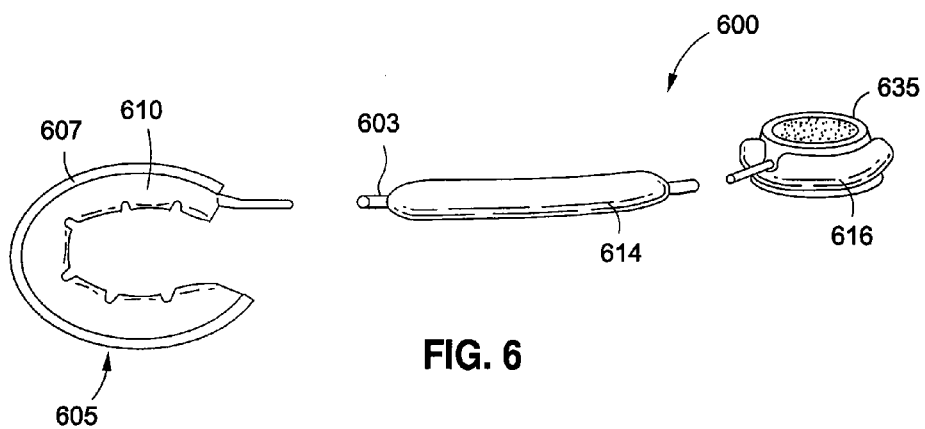
FIG. 6 illustrates an exploded, perspective view of another self-adjusting gastric banding system having various compliant components according to an embodiment of the present invention.

With reference to FIGS. 5 and 6, and in accordance with various embodiments, a tube compliant component 514, 614 may be fluidly coupled to the tubing 503, 603. As illustrated in FIG. 6, the compliant component 614 may run along substantially the entire length of the tubing 603. In another embodiment, as illustrated in FIG. 5, the compliant component 514 may be limited to a smaller section of the entire length of the tubing 503. The compliant component 514, 614 may be fluidly coupled to the tubing 503 at one or more locations. For example, with reference to FIG. 6, the compliant component 614 and the tubing 603 may be perforated to allow for efficient transfer of the fluid between the tubing 603 and the compliant component 614.

In another embodiment, the tubing 603 itself may be compliant, and the durometer, thickness, and/or diameter of the tubing 603 may be altered to achieve a desired degree of compliance. Other components of the gastric band 605 may similarly have altered properties in order to achieve a desired degree of compliance.

In an embodiment, where the tube compliant component 514, 614 facilitates automated adjustment of the gastric band 505, 605, the compliant component 514, 614 may have features configured to resist kinking and/or leakage of the tubing 503, 603. For example, the compliant component 514, 614 may include rigid portions (e.g., similar to a skeleton) and flexible portions. The rigid components may give structure to the compliant component 514, 614 and/or the tubing 503, 603 to prevent kinking and/or leakage due to external forces on the compliant component 514, 614 and/or the tubing 503, 603. The flexible components may automatically expand in response to an increased pressure in the inflatable portion 510, 610 of the gastric band 505, 605.

In accordance with another embodiment, and with continued reference to FIGS. 5 and 6, the access port 535, 635 may be fluidly coupled to a port compliant component 516, 616. As illustrated in FIG. 5, the compliant component 516 may be a balloon, reservoir, or other expandable device that is adjacent to the port 535. In an embodiment as illustrated in FIG. 6, the compliant component 616 may substantially surround the access port 635. The compliant component 616 may be fluidly coupled to the access port 635 at a single location near a coupling between the tubing 603 and the access port 635. In another embodiment, the compliant component 616 may be fluidly coupled to the access port 635 at multiple locations.

As noted above, any combination of the inflatable portion 510, 610, the compliant component 512, the compliant ring 407, the tube compliant component 514, 614, and/or the port compliant component 516, 616 may be used in accordance with various embodiments. When the pressure in the inflatable portion 510, 610 exceeds a predetermined pressure, the compliant components 407, 512, 514, 516, 614, 616, in any particular configuration or combination, expand to receive an amount of the fluid from the inflatable portion 510, 610 via the inflatable portion 510, 610, the tubing 503, 603, and/or the access port 535, 635, and/or to reduce the constriction formed by the gastric band 405, 505, 605. The predetermined pressure may be predetermined based on a pressure that would indicate an obstruction is attempting to pass through the constriction caused by the gastric band 405, 505, 605.

The compliant components 407, 512, 514, 516, 614, 616 described herein, in accordance with various embodiments, may be designed with an expansion pressure at which pressure the components 407, 512, 514, 516, 614, 616 begin to expand, to receive fluid from the inflatable portion 510, 610 of the gastric band 505, 605, and/or to reduce the constriction formed by the gastric band 405, 505, 605. The expansion pressure may be configured to correspond to a predetermined pressure in the inflatable portion 410, 510, 610 that may indicate an obstruction exists in the esophageal-gastric junction.

For example, the obstruction may result in a large spike in intra-esophageal pressure that exceeds the expansion pressure and causes the compliant components to expand and receive fluid from the inflatable portion 510, 610. The reduction in fluid in the inflatable portion 510, 610 causes the constriction around the patient's stomach to loosen, in order to relieve the spike in pressure and allow the obstruction to pass through the esophageal-gastric junction. When the obstruction passes, the increased pressure in the inflatable portion 510, 610 is reduced, and the fluid flows back into the inflatable portion 510, 610 due to the elasticity of the compliant components 512, 514, 516, 614, 616, to restore the original amount of constriction of the gastric band 505, 605. This change in constriction of the gastric band 505, 605 results or is achieved without the use of flow rate limiting devices or valves.

Figure 7:
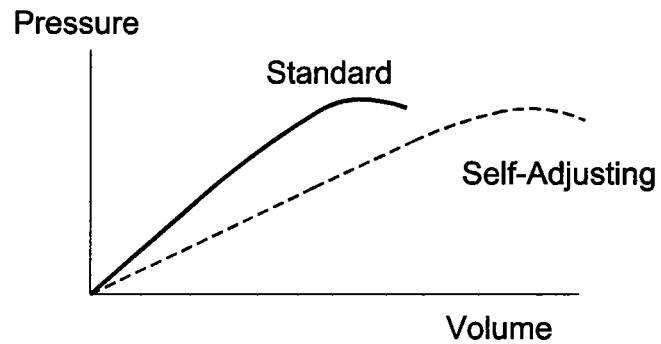
FIG. 7 illustrates a chart showing pressure-volume curves for a standard gastric band and a self-adjusting gastric band according to an embodiment of the present invention.

The graph in FIG. 7 illustrates, according to various embodiments, the effect the compliant components described herein have on the pressure in the gastric banding system. As can be seen in FIG. 7, a standard gastric banding system without compliant components has a certain pressure-volume relationship. After the gastric banding system is flushed with saline to remove any air trapped within the system (e.g., in the gastric band, the tubing, and the port), the pressure-volume relationship generally takes the form illustrated by the "Standard" curve in FIG. 7. The dashed "Compliant" curve illustrates an example embodiment of the pressure-volume relationship for a gastric banding system with one or more compliant components. As illustrated, the self-adjusting gastric banding system may include a greater volume of saline than a standard gastric banding system for a given level of pressure.

Figure 8:
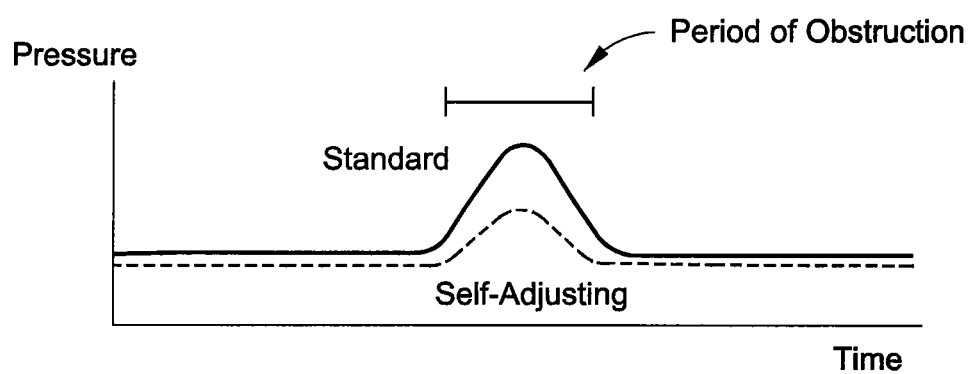
FIG. 8 illustrates a chart showing pressure-time curves for a standard gastric band and a self-adjusting gastric band subject to a period of obstruction according to an embodiment of the present invention.

The graph in FIG. 8 illustrates, according to various embodiments, pressure characteristics of a "Standard" gastric banding system and a "Self-Adjusting" gastric banding system during use of the systems in a patient. Initially, the two systems are set to the same operating pressure, for example, for a desired level of constriction of the patient's stomach. As a large bolus of food or some other obstruction encounters the gastric band, the pressure in each system increases. As illustrated, the standard system has a larger pressure increase during the period of obstruction than the self-adjusting gastric banding system experiences. This smaller increase in pressure, according to various embodiments, is due to the addition of the reservoir space in the compliant component(s). As pressure in the gastric banding system increases, fluid is transferred into the reservoir space. Once the obstruction passes, the fluid is automatically returned from the reservoir space back into the gastric band.

The various compliant components disclosed herein may have any shape or configuration that facilitates removing an amount of fluid from the inflatable portion of the gastric band in response to an increased pressure in the inflatable portion. For example, the compliant components may be selected from a compressible reservoir, an elastic polymer, a balloon, a rubber container, a silicone container, a collapsible container, a bellows, and combinations thereof that are configured to contain the fluid.

Examples of self adjusting gastric banding systems now having been described, attention will be turned to gastric banding systems with a satiety booster. Occasionally, the patient may desire a little extra help from the gastric band system to avoid overeating. This extra appetite suppression may be achieved by the patient intentionally pressing on an implanted bladder which provides a satiety boost by transfer fluid within the implanted bladder to an inflatable portion of the gastric band, thereby tightening the gastric band and causing the patient to feel full.

Figure 9:
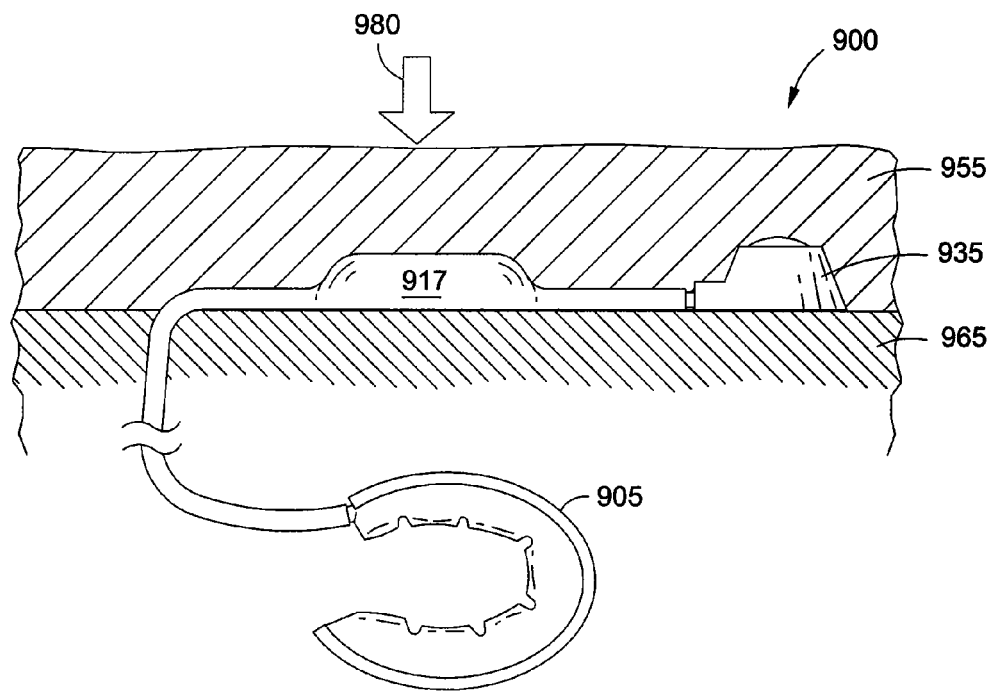
FIG. 9 illustrates a gastric banding system with a satiety boosting bladder according to an embodiment of the present invention.

In one embodiment, FIG. 9 illustrates a gastric band system 900 which may include a gastric band 905 in fluid communication with a bladder 917 and a port 935. The gastric band system 900 may be implanted between the skin 955 of the patient and the rectus muscle fascia 965. When a patient desires to temporarily suppress appetite, the patient may press on the patient's skin near the location of the bladder 917 as designated by arrow 980. As a patient presses at the location of the arrow 980, pressure may be exerted on the bladder 917, causing fluid from the bladder 917 to be transferred to the gastric band 905, thereby tightening the gastric band 905.

In one embodiment, the gastric band 905 and the port 935 may be implanted as usual with the bladder 917. However, an additional step may be added to the implantation procedure so that a surgeon may tunnel an extra pouch between the skin 955 and the rectus muscle fascia 965. The extra pouch may be positioned under the subcutaneous fat or on top of the subcutaneous fat and the bladder 917 may be positioned within the tunneled pouch. Following surgery, the gastric band 905 may be adjusted as usual by inserting a needle into the access port 935 and adding fluid as necessary. Once the proper adjustment has been made, the patient may feel or experience significantly increased satiety. If the patient feels hungry during a period which their physician has deemed inappropriate (e.g., between normal size meals), the patient may want to temporarily suppress their appetite by pressing on the skin near the arrow 980, as discussed above.

Figure 10:
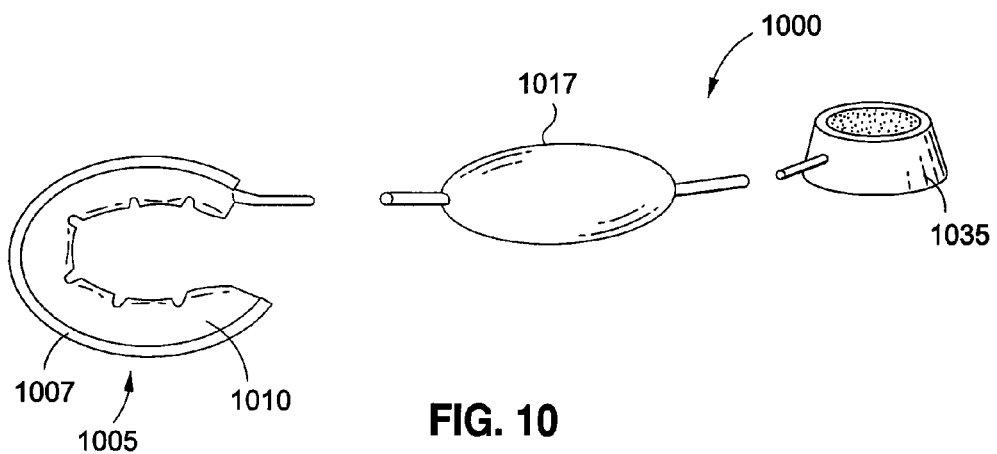
FIG. 10 illustrates an exploded, perspective view of a gastric banding system having a satiety boosting bladder according to an embodiment of the present invention.

FIG. 10 illustrates one embodiment of a gastric band system 1000. As shown, the gastric band system 1000 may include a gastric band 1005 comprising an inflatable portion 1010 in a compliant ring 1007. The gastric band 1005 may be in fluid communication with the bladder 1017 which in turn may be in fluid communication with an access port 1035. As shown, the bladder 1017 may be of an ellipsoidal shape and may be located between the gastric band 1005 and the access port 1035. However, other placements of the bladder 1017 may be possible.

Figure 11:
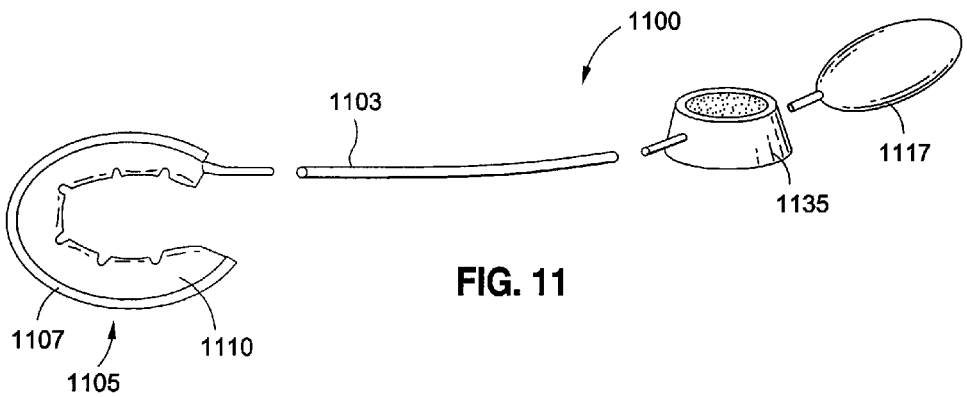
FIG. 11 illustrates an exploded, perspective view of another gastric banding system having a satiety boosting bladder according to an embodiment of the present invention.

FIG. 11 illustrates an example of one embodiment where a bladder 1117 is attached on the other side of the access port 1135. As shown, the gastric band system 1100 may include a gastric band 1105 with an inflatable portion 1110 and a ring 1107. The gastric band 1105 may be connected to a tubing 1103 which may be connected to the access port 1135. As shown, when the patient presses on his or her skin at a location near the bladder 1117, fluid within the bladder 1117 may travel through the access port 1135 and the tubing 1103 and into the inflatable portion 1110 of the gastric band 1105, thereby increasing the amount of fluid within the gastric band 1105 and causing the patient to feel satiety.

Figure 12:
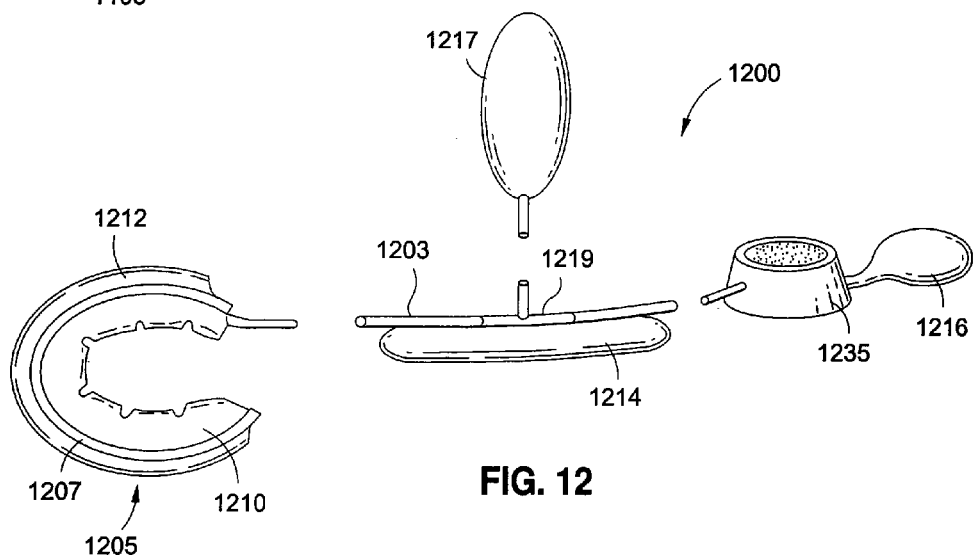
FIG. 12 illustrates an exploded, perspective view of a gastric banding system having a "T-connected" satiety boosting bladder according to an embodiment of the present invention.

In one embodiment as shown in FIG. 12, the bladder 1217 may be connected to the gastric banding system 1200 through a "T" connector 1219 such that the bladder 1217 is not in-line with the port 1235 nor the gastric band 1205. In this manner, the "T" connector 1219 may be a part of the tubing 1203 and may allow the bladder 1217 to be in fluid communication with other portions of the gastric banding system 1200 such as a tube component 1214 and an end compliant portion 1216, among other components.

Other methods of fluidly connecting a bladder (e.g., bladder 1217) to a gastric band (e.g., a gastric band 1205) may be possible. For example, a "Y" connector (not shown) or any other type of connector may be used.

Figure 13:
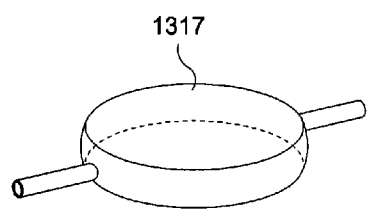
FIG. 13 illustrates a circular satiety boosting bladder according to an embodiment of the present invention.
Figure 14:
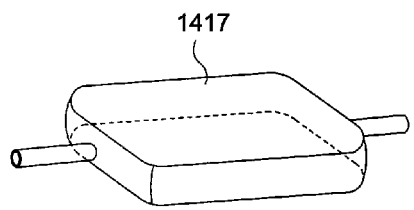
FIG. 14 illustrates a rectangular satiety boosting bladder according to an embodiment of the present invention.

Although bladders 1017, 1117, and 1217 in FIGS. 10, 11 and 12 respectively have been shown to be ellipsoidal, other shapes may be possible. For example, FIG. 13 illustrates a flat, circular bladder 1317 while FIG. 14 illustrates a rectangular bladder 1417. The bladders 1317 and 1417 may be implemented anywhere, for example, as bladder 1017 between the gastric band 1005 and the port 1035, or as bladder 1117 coupled to the port 1135. In addition, other shapes may be possible such as a spherical bladder, a prolate spheroid, an oblate spheroid or other suitable shapes (not shown).

The previous bladder shapes, for example, bladders 1017, 1117, 1317 and 1417 may be useful within a limited range of pressures. However, as the pressure within the fluid increases, these bladders 1017, 1117, 1317 and 1417 may bulge and take on a more spherical shape. The bulging characteristics may be reduced or limited by choosing particular combinations of materials and shapes.

Figure 15:
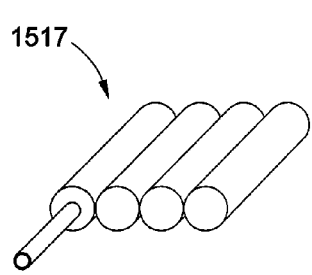
FIG. 15 illustrates a series of cylindrical bladders according to an embodiment of the present invention.
Figure 16:
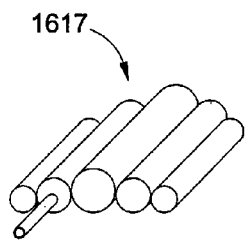
FIG. 16 illustrates a series of differently sized cylindrical bladders according to an embodiment of the present invention.
Figure 17:
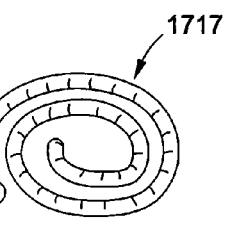
FIG. 17 illustrates a coiled bladder according to an embodiment of the present invention.

Examples of non-bulging bladder shapes are illustrated in FIGS. 15, 16 and 17.

As shown in FIG. 15, bladder 1517 may include a series of connected cylinders having similar shapes and similar sizes. While shown here to be four cylinders, any number of cylinders in series may be possible. The series of connected cylinders of the bladder 1517 may be in fluid communication with each other (e.g., a gap may exist proximal to the point of attachment thereby allowing fluid to be freely transferred between the different cylinders of the bladder 1517). In one embodiment, when a flexible non-stretching material such as polytetrafluoroethylene (PTFE) is formed into a series of connected cylinders, the bladder 1517 may be inflated to its maximum volume and shape. As more fluid is injected into the bladder 1517, the pressure in the system dramatically increases but the shape of the bladder 1517 does not stretch and expand.

FIG. 16 illustrates a bladder 1617 comprising a series of cylinders of various sizes. Again, while shown here to be five cylinders, any number of cylinders in the series may be possible. As shown, the diameter of the middle cylinder of the bladder 1617 may be larger, while the diameter of the outer cylinders may be smaller. Similar to the bladder 1517 of FIG. 15, when a flexible non-stretching material such as PTFE is formed into a series of connected cylinders, the bladder 1617 may be inflated to its maximum volume and shape. As more fluid is injected into the bladder 1617, the pressure in the system dramatically increases but the shape of the bladder 1617 does not stretch and expand.

FIG. 17 illustrates a coil-like bladder 1717. The bladder 1717 may include internal structures that allow the bladder

1717 to inflate (i.e., allowing the diameter of the coils of the bladder 1717 to increase) but without substantially altering the shape of the bladder 1717 (i.e., preventing the bladder 1717 from "uncoiling"). As such, the patient may press on any portion of the bladder 1717 to obtain a boost in satiety.

While different shapes may be possible to construct the bladder, bladder devices are not designed to encourage needle insertion. For example, bladders 1017, 1117, 1317, 1417, 1517, 1617, and 1717 may be constructed out of puncture-resistant fabrics or hard shells to protect the bladders 1017, 1117, 1317, 1417, 1517, 1617, and 1717 from needle punctures. Additionally, the bladders 1017, 1117, 1317, 1417, 1517, 1617, and 1717 may be made resistant to needle punctures by being positioned away from an injection port (e.g., injections ports 1035, 1135).

In one embodiment, the bladders 1017, 1117, 1317, 1417, 1517, 1617, and 1717 may be constructed out of flexible materials such as rubber, silicone, latex and the like and/or thin plastics such as polyethylene (PE), polyethylene terephthalate (PET), polycarbonate (PC), polypropylene (PP), polyamides (PA), PTFE, polyvinyl chloride (PVC), polysulfone (PSU), polyphenylsulfone (PPSU), polyetheretherketone (PEEK), among other fabrics or materials.

Figure 18:
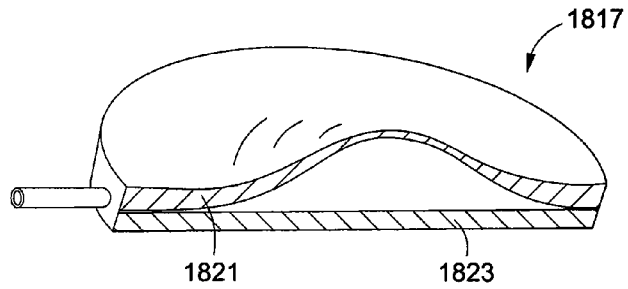
FIG. 18 illustrates a cross-sectional view of a satiety boosting bladder according to an embodiment of the present invention.

While different shapes of bladders have been discussed, the walls within each of the bladders (e.g., the bladders 1017, 1117, 1317, 1417, 1517, 1617, and 1717) may also vary. For example, as shown in FIG. 18, the bladder 1817 may include a tapered wall 1821 shown as the top wall and a uniform wall 1823 shown as a bottom wall. The bladder 1817 of FIG. 18 may be constructed with a tapered wall thinnest at the center of the bladder 1817 where most of the fluid is stored. When the center of the bladder 1817 is pressed, the fluid may be released in an efficient manner instead of being dispersed to the edges of the bladder 1817. However, in certain embodiments, bladders with uniform wall thicknesses throughout may also be possible.

The bladders 1017, 1117, 1317, 1417, 1517, 1617, 1717, and 1817 described herein may be used in conjunction with each other and with other bladders of varying compliance. For example, referring back to FIG. 12, the bladder 1217 may be a non-compliant component and may be used to achieve fluid flow when the patient presses on the bladder 1217. The bladder 1216 may be a compliant component and may be used as an intentional fluid flow creator and as a pressure moderating device. These two bladders 1217 and 1216, among other bladders, may also be used simultaneously such that one non-compliant bladder 1217 may allow for fluid transfer while the other compliant bladder 1216 may act as a pressure monitoring device.

In one or more embodiments, bladders 1017, 1117, 1317, 1417, 1517, 1617, 1717, and 1817 may allow for fluid transfer via one or more mechanisms. Fluid transfer may be intentionally induced when the patient consciously presses on the bladder (e.g., bladders 1017, 1117, 1317, 1417, 1517, 1617, 1717, and 1817) by hand. Fluid transfer may also be unintentionally induced when the patient undergoes daily movement (e.g., stretching, walking, breathing, talking) as these actions may cause pressures on the bladders (e.g., the bladders 1017, 1117, 1317, 1417, 1517, 1617, 1717, and 1817) as well.

In one embodiment, when a patient presses on the bladder 1217 to cause fluid to flow towards the gastric band 1205, the gastric banding system 1200 may be configured to permit the fluid to flow back to the bladder 1217 at a substantially unimpeded rate.

In another embodiment, a flow rate restriction device may be implemented into the bladder 1217 to restrict or control the fluid flow between the bladder 1217 and the gastric band 1205.

Figure 19:
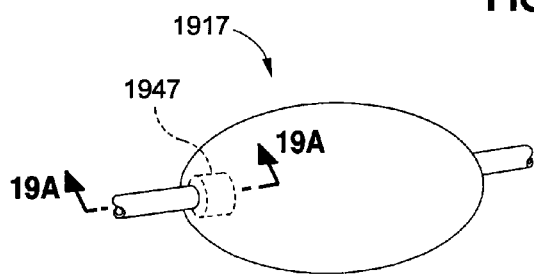
FIG. 19 illustrates a bladder having a flow control mechanism according to an embodiment of the present invention.
Figure 19A:
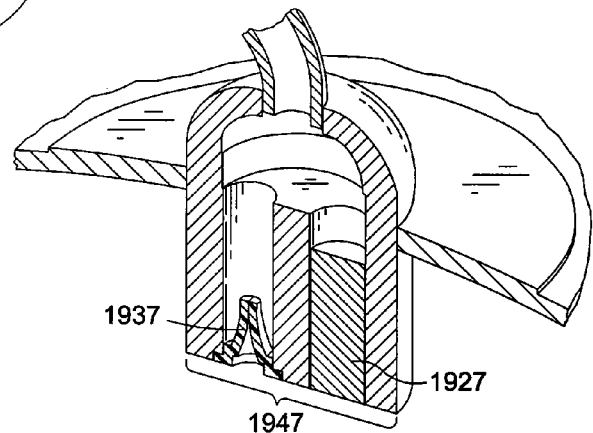
FIG. 19A illustrates a close up view of the flow control mechanism of FIG. 19 according to an embodiment of the present invention.

FIG. 19 illustrates one embodiment of a flow rate restriction device 1947 within a bladder 1917. FIG. 19A illustrates a close up view of the restriction device 1947. As shown, the flow rate restriction device 1947 may include a flow restrictor 1927 and a duckbill valve 1937 located proximately at an area where a tubing is joined to the bladder 1917. When the patient presses on the bladder 1917, fluid may flow out of the duckbill valve 1937 at one rate and when fluid flows from the gastric band (not shown) back into the bladder 1917, the flow restrictor 1927 may control the flow of the fluid at a second rate.

In one embodiment the rate that fluid leaves the bladder 1917 through the duckbill valve 1937 may be higher than the rate that fluid flows through the flow restrictor 1927 back into the bladder 1917. Conversely, the flow rate of fluid entering the bladder 1917 through the duckbill valve 1937 may be higher than the flow rate of fluid leaving the bladder 1917. Alternatively, the flow rates may be equal.

While a duckbill valve 1937 and a flow restrictor 1927 have been illustrated in FIG. 19, other forms of restriction may be possible.

Unless otherwise indicated, all numbers expressing quantities of ingredients, volumes of fluids, and so forth as used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of and/or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A self-adjusting gastric band for the treatment of obesity that adjusts to provide a satiety boost to a patient, the self-adjusting gastric band comprising:
    an inflatable portion disposable about an esophageal-gastric junction of the patient;
    an access port fluidly coupled to the inflatable portion via tubing to fill and drain the inflatable portion;
    a satiety boosting bladder fluidly coupled to the inflatable portion and the access port, wherein the satiety boosting bladder transfers fluid to the inflatable portion in response to an inwardly directed force effectable by the patient and exerted on the satiety boosting bladder; and
    a fluid flow rate controlling device, including:
        a one-way valve that controls fluid flow from the satiety boosting bladder at a first flow rate, and
        a flow restrictor that controls fluid flow into the satiety boosting bladder at a second flow rate different from the first flow rate, wherein the first and second flow rates are non-zero flow rates.

2. The gastric band of claim 1 further comprising a compliant portion coupled to at least one of the inflatable portion, the access port, the tubing or the satiety boosting bladder, the compliant portion configured to automatically relax the constriction formed by the gastric band and allow a large bolus to pass through the constriction.

3. The gastric band of claim 2 further comprising a ring coupled to the inflatable portion for providing structure and support to the inflatable portion, wherein the ring facilitates disposing the inflatable portion about the esophageal-gastric junction.

4. The gastric band of claim 1 wherein the satiety boosting bladder is configured to transfer fluid to the inflatable portion in response to the patient pressing on the area of skin closest to the satiety boosting bladder.

5. The gastric band of claim 1 wherein the satiety boosting bladder is configured to transfer fluid to the inflatable portion in response to the patient breathing, talking, or moving.

6. The gastric band of claim 1 wherein the satiety boosting bladder is ellipsoidal, circular, or rectangularly shaped.

7. The gastric band of claim 1 wherein the satiety boosting bladder is a series of uniformly sized cylindrical bladders, a series of non-uniformly sized cylindrical bladders, or a coiled bladder.

8. The gastric band of claim 1 wherein the satiety boosting bladder is located between a skin layer and a rectus muscle fascia layer within a body of the patient.

9. The gastric band of claim 1 wherein the satiety boosting bladder comprises a wall of varying thickness.

10. The gastric band of claim 9 wherein the wall comprises a tapered portion near the center of the satiety boosting bladder.

11. The gastric band of claim 1 wherein the satiety boosting bladder is fluidly coupled to the inflatable portion and the access port via a "T-connector".

12. The gastric band of claim 1 wherein the satiety boosting bladder is fluidly coupled to the inflatable portion and the access port via a "Y-connector".

13. The gastric band of claim 1 wherein the satiety boosting bladder is further configured to receive fluid from the inflatable portion.

14. The gastric band of claim 1, wherein the fluid flow rate controlling device is within the satiety boosting bladder.

15. A self-adjusting gastric band for the treatment of obesity that adjusts to provide a satiety boost to a patient, the self-adjusting gastric band comprising:
    an inflatable portion disposable about an esophageal-gastric junction of the patient;
    an access port fluidly coupled to the inflatable portion via tubing to fill and drain the inflatable portion;
    a satiety boosting bladder fluidly coupled to the inflatable portion and the access port; and
    a fluid flow rate controlling device within the satiety boosting bladder, including
        a one-way valve that controls fluid flow from the satiety boosting bladder at a first flow rate, and
        a flow restrictor that controls fluid flow into the satiety boosting bladder at a second flow rate different from the first flow rate, wherein the first and second flow rates are non-zero flow rates.

* * * * *